(12) United States Patent
Healey et al.

(10) Patent No.: US 6,890,182 B2
(45) Date of Patent: May 10, 2005

(54) METHOD AND APPARATUS FOR THE SELECTION OF ORAL CARE CHEMISTRY

(75) Inventors: Patrick John Healey, West Chester, OH (US); Scott Matthew Wright, Cincinnati, OH (US); Louis John Viltro, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/205,232

(22) Filed: Jul. 25, 2002

(65) Prior Publication Data

US 2004/0018475 A1 Jan. 29, 2004

(51) Int. Cl.[7] ............................................... G09B 25/00
(52) U.S. Cl. ...................................... 434/365; 434/367
(58) Field of Search ................................ 434/365, 367, 434/377, 382, 429, 430, 262, 263, 433; 600/300

(56) References Cited

U.S. PATENT DOCUMENTS

| | | |
|---|---|---|
| 368,373 A | 8/1887 | Blinn |
| 730,040 A | 6/1903 | McKinley et al. |
| 904,190 A | 11/1908 | Fesler |
| 1,060,524 A | 4/1913 | Wolfe |
| 1,809,330 A | 6/1931 | Dorrance et al. |
| 3,187,360 A | 6/1965 | Spohr |
| 3,217,720 A | 11/1965 | Cyzer |
| 3,907,441 A | 9/1975 | Idec et al. |
| 3,927,435 A | 12/1975 | Moret et al. |
| 4,013,370 A | 3/1977 | Gingras |
| 4,019,654 A | 4/1977 | Van Manen |
| 4,046,288 A | 9/1977 | Bergman |
| 4,060,870 A | 12/1977 | Cannarella |
| 4,071,300 A | 1/1978 | Nichols et al. |
| 4,139,114 A | 2/1979 | Long et al. |
| 4,160,271 A * | 7/1979 | Grayson et al. ............... 700/90 |
| 4,434,810 A | 3/1984 | Atkinson |
| 4,693,622 A | 9/1987 | Booth |
| 4,750,151 A * | 6/1988 | Baus ........................... 700/90 |
| 4,895,276 A | 1/1990 | Maldonado |
| 4,948,737 A | 8/1990 | Quenin et al. |
| 5,058,230 A | 10/1991 | Hodosh et al. |
| 5,088,850 A | 2/1992 | Taichman et al. |
| 5,100,252 A | 3/1992 | Podolsky |
| 5,226,206 A | 7/1993 | Davidovitz et al. |
| 5,276,932 A | 1/1994 | Byrd |
| 5,289,604 A | 3/1994 | Kressner |
| 5,309,590 A | 5/1994 | Giuliani et al. |
| 5,351,186 A * | 9/1994 | Bullock et al. ................. 705/1 |
| 5,353,460 A | 10/1994 | Bauman |
| 5,383,242 A | 1/1995 | Bigler et al. |
| 5,476,384 A | 12/1995 | Giuliani et al. |
| 5,504,959 A | 4/1996 | Yukawa et al. |

(Continued)

FOREIGN PATENT DOCUMENTS

| | | |
|---|---|---|
| DE | 93 16316.9 | 2/1994 |
| FR | 2 700 678 | 7/1994 |
| GB | 2 307 674 A | 6/1997 |

*Primary Examiner*—Kurt Fernstrom
(74) *Attorney, Agent, or Firm*—Peter D. Meyer (57) ABSTRACT

A method and apparatus for the selection of oral care chemistries by a consumer from a plurality of available options. An oral care selection advisor first requests information from a consumer regarding their oral care preferences. The oral care selection advisor then selects a classification of chemistries from among at least two available classifications corresponding to those oral care preferences. The information is then displayed from the oral care selection advisor identifying at least one chemistry within the selected classification, allowing the consumer to identify the chemistries corresponding to the consumer's oral care preferences.

14 Claims, 4 Drawing Sheets

U.S. PATENT DOCUMENTS

| | | | |
|---|---|---|---|
| 5,821,872 A | * 10/1998 | Brown et al. | 340/5.91 |
| 5,842,487 A | 12/1998 | Ledet | |
| 5,881,920 A | 3/1999 | Seager et al. | |
| 5,909,977 A | 6/1999 | Kuo | |
| 5,943,723 A | 8/1999 | Hilfinger et al. | |
| 5,991,921 A | 11/1999 | Saito | |
| 5,997,201 A | 12/1999 | Bossert et al. | |
| 6,058,367 A | * 5/2000 | Sutcliffe et al. | 705/1 |
| 6,280,775 B1 | * 8/2001 | Sasson et al. | 424/616 |
| 6,304,855 B1 | * 10/2001 | Burke | 705/27 |
| 6,368,113 B1 | * 4/2002 | Unger et al. | 434/429 |
| 6,516,245 B1 | 2/2003 | Dirksing et al. | |
| 6,533,418 B1 | * 3/2003 | Izumitani et al. | 351/204 |
| 6,555,094 B1 | * 4/2003 | Glandorf et al. | 424/52 |

* cited by examiner

METHOD AND APPARATUS FOR THE SELECTION OF ORAL CARE CHEMISTRY

FIELD OF THE INVENTION

The present invention is directed to the methods and apparatus for the consumer selection of at least one type of oral care chemistry from a plurality of options.

BACKGROUND OF THE INVENTION

A wide variety of oral care chemistry products are currently available in the market place. Typically, these products comprise at least two characteristics, or attributes, such as flavor and cleansing. Other characteristics can include texture (i.e. gel, paste, etc.) and appearance (i.e. mono-color, striped, sparkles, etc.). However, in a given oral care product, all of these characteristics must be combined to give the oral care product a specific character, range of effectiveness, result(s), and consumer experience.

There has been a great increase in the popularity of 'premium' chemistries. The 'premium' chemistries tend to be more expensive to produce and purchase than 'non-premium' chemistries. Many consumers are willing to pay an increased price for such premium chemistries in order to enjoy an oral care chemistry that more particularly suits their preferences, or needs, or that offers a greater variety of options than typically available in 'non-premium' chemistries.

Because of increased price or special ordering requirements, however, many consumers may find experimentation or the 'trial and error' associated with finding their most desired or effective type of oral care chemistry to be unacceptable. Many consumers do not understand how the various options correspond to their preferences or needs. Further complicating this situation is that in a given store, dozens of oral care chemistry options are available. Even further complicating this situation is that many different types of oral care chemistries have names or designations that can sound or appear confusingly similar to the consumer. Because of this confusion, the consumer is often unable to distinguish between different oral care chemistries or in some cases selects a different item than what the consumer intended.

The positive or negative reaction to a particular oral care product by a consumer is described as the product's 'acceptance'. Whether or not a given consumer will 'accept' a given oral care product is a matter of taste, which is, of course, subjective.

It is, therefore, desirable to provide a method and apparatus that can allow a consumer to identify one or more oral care products in which that consumer may have a greater chance of accepting than other available oral care chemistries. Such a method and apparatus should be simple to understand and use, yet provide for preference and/or needs matching. The methods and apparatus of the present invention are particularly well suited to assist the selection of oral care chemistry products, particularly premium oral care products.

SUMMARY OF THE INVENTION

The present invention provides a method for the selection of an oral care treatment by a consumer from a plurality of options comprising the step of first, requesting information from a consumer regarding that consumer's oral care preferences with an oral care selection advisor. The oral care selection advisor selects a classification of chemistries from among at least two available classifications, each classification comprising one or more different chemistries. Each of the available classifications corresponds to the consumer's oral care preferences. Information is displayed from the oral care selection advisor identifying the chemistry within the selected classification, thereby allowing the consumer to identify the chemistries corresponding to the consumer's oral care preferences.

The present invention also provides a method for the selection of an oral care treatment from a plurality of options comprising the steps of first, providing at least two available classifications of chemistries. Next, selecting an oral care device having at least one compartment, the compartment corresponding to a classification of chemistries from among at least two available classifications, disposed therein. Each classification comprises at least one chemistry corresponding to a consumer's oral care preferences. Then, the chemistry is placed into the compartment.

DETAILED DESCRIPTION OF THE INVENTION

As used herein, "chemistry," "chemistries," or "chemistry(s)" means at least one material or substance that either singly, or in combination, can deliver a planned product usable to obtain a desirable oral care result (i.e., breath freshening, tooth cleaning, tooth whitening, tooth brightening, gum treatment, tooth surface sealing, tartar control, etc.).

As used herein, "consumer-based selections" can be aspirationally-derived or preference-derived. An aspirationally-derived consumer-based selection involves the consumer selection of one or more chemistry(s) from a plurality of options based on the consumer's desire to achieve one or more improvements to his/her lifestyle (i.e., reduced fear of conversation while in close proximity to another person, reduced fear of smiling in photographs, etc.). A preferentially-derived consumer-based selection involves the consumer's (including any other third party) selection of one or more chemistry(s) from a plurality of options based on personal likes, dislikes, and desires of the characteristics of each option (i.e., prefer mint, dislike tomato, want whitening, do not want tarter control, need gum medication, do not need sensitivity reduction, etc.).

As used herein, "flavor" means the property or quality of something that affects the sense of taste in the mouth.

As used herein, "hardware-based" means interaction to reach information contained, formulated, and delivered entirely via non-electric or electronic means. Hardware can be static (i.e., a flow chart or matrix chart), or dynamic (i.e., one or more dials, slides, drums, or the like, moved into a particular arrangement or place so as to produce one or more instructions or selections for the consumer).

As used herein, the term "oral care device" refers to a brushing system, including a multiple cartridge dispensing system, that can dispense oral care products either directly onto brush bristles, through the brush to the bristles, directly into the mouth, onto applicators, into toothpaste, oral rinse, oral cavity strips, or other topical treatments. A multiplicity of oral care products may be provided to the cartridges for use in brushing.

As used herein, the term "oral care preferences" refers to the stated, perceived, and/or medically recommended chemistry(s) for an individual, with respect to the characteristics of an oral care treatment. Preferences may also include information not directly related to oral care attributes, but can serve as a proxy for these attributes. For example, the requested oral care preference information may include information pertaining to the consumer's lifestyle interests (e.g., hobbies and other preferred activities), recent purchase patterns (e.g., food and beverage preparation appliances), medical needs (e.g., prescriptions), and the like. By way of example, a consumer who regularly participates in activities such as mountain biking and sea kayaking, and who also enjoys South American travel, may have a remarkably different oral care preference from another consumer with similar demographic characteristics (e.g., age, ethnicity, education, income) who regularly watches televised sporting events and does not like to travel. Each may have a different preference than another consumer who has sought professional medical advice to address a particular oral care health issue.

As used herein, the term "oral care products" is defined as particular types of chemistry(s) that can be combined to produce an "oral care treatment regimen" by the consumer. The oral care treatment regimen may comprise chemistry(s) from one or any number of attribute classifications.

As used herein, "software-based" means interaction to reach information contained, formulated, and delivered with devices in which one or more are electric or electronic in construction and require software code for operation. The software can be locally installed into one or more devices or remotely located.

As used herein, "store-based" means an interaction between the consumer and information utilizing devices or information source elements occurring at the point of purchase (e.g., store, dentist office, on-line, mobile van, etc.).

As used herein, "treatment regimen" means the techniques and/or actions comprised of methods and chemistry(s) that are applied in a specified situation, fashion, and duration, for at least one application. A treatment can be used for general oral care including, but not limited to, care of the teeth and gums.

As used herein, "web-based" means an interaction between a consumer and information based on communication, either in near real time or by delayed transmission, between two points, in which this connection uses in part the Internet, commonly referred to as the World-Wide-Web, where a consumer is at one of the points. The consumer located point can be a store or non-store location (i.e., home or office) for such a web-based interaction.

Certain information regarding the oral care preferences of a consumer may be used to assist the consumer in the selection of at least one chemistry from an available group to provide an oral care treatment regimen. The method of the present invention centers on the ability to properly identify oral care preferences for a consumer and match these preferences with an appropriate chemistry(s) to formulate an oral care treatment regimen.

Specifically, certain key pieces of information regarding the oral care preferences of a consumer can be used to assist that individual in the selection of classifications of chemistry(s) which are particularly adapted to satisfy the consumer's oral care preferences. The use of chemistry(s) within such adapted classifications can increase the acceptance of such products by consumers compared to self-selection without assistance of the present method.

The various chemistries of an oral care treatment regimen can be separated into different classifications or categories. The consumer can be prompted in any suitable manner (e.g., through the answering of questions printed on a chart or interactive display screen, etc.) to yield information sufficient to provide the consumer with a selection of any particular chemistry. As a non-limiting example, consumers may be asked whether they desire control of dental calculus build-up. In this example, the oral care preference with respect to any particularized chemistry is determined directly. It has been found that consumers are generally adept at accurately identifying their preferred oral care treatment regimens. Thus, in specific embodiments of the present invention, such information can be collected directly from the consumer. In variations of this embodiment, fewer options may be provided to the consumer. Further, it is believed that a prescribed avenue of treatment can direct a consumer (i.e., as prescribed by an oral care health advisor) to identify, and purchase, preferred oral care classifications.

In an exemplary, but non-limiting, embodiment, the present invention comprises the basic steps of: requesting information from a consumer regarding the consumer's oral care preferences and/or aspirations, selecting an appropriate classification of chemistries from a group of two or more available classifications of chemistries, and displaying information to the consumer identifying the chemistries which make up the selected classifications of chemistries allowing the consumer to identify, and optionally purchase, chemistries within the selected classification. In certain embodiments of the present invention, the basic steps of requesting information from a consumer regarding the consumer's oral care preferences and/or aspirations and selecting an appropriate classification of chemistries are performed in a substantially continuous, interactive process.

For example, a store display could be equipped with an interactive computer which can prompt the user to answer questions, keep track of the answers, provide new questions and/or selections based upon the answers provided, and select an appropriate classification based on those answers as described above. In alternative embodiments, the information may be collected from a consumer though the use of an interactive site on the World Wide Web, an interactive menu-driven phone system, and the like. Charts, tables or other figures may be used as devices for requesting information from a consumer and taking the consumer through the oral care preference process as described above. Similarly, charts, figures, and the like, can be published in publications such as newspapers or magazines, mailings, in-store displays or advertising, distributed via e-mail, published over a network such as the World Wide Web, and the like.

It is also possible for information regarding the selection of oral care chemistries in accordance with the methods of the present invention to be distributed to doctors, dentists, dental hygienists, dental colleges, merchants, or other persons and/or places likely to be engaged in the recommendation, retail sale, promotion, distribution, giveaway, or trade of oral care products and/or chemistries. The interaction described in the present application could take place between a purchasing agent, consumer, end-user, a consumer's caretaker, a consumer's parent, a consumer's dentician, a consumer's insurer, and a consumer's health care professional, merchant, or other person engaged in the sale of oral care products and/or chemistry(s). Further, oral care chemistry selection may occur proximate to a display case containing one or more of the chemistries available within each of any available classifications.

Figure 1:
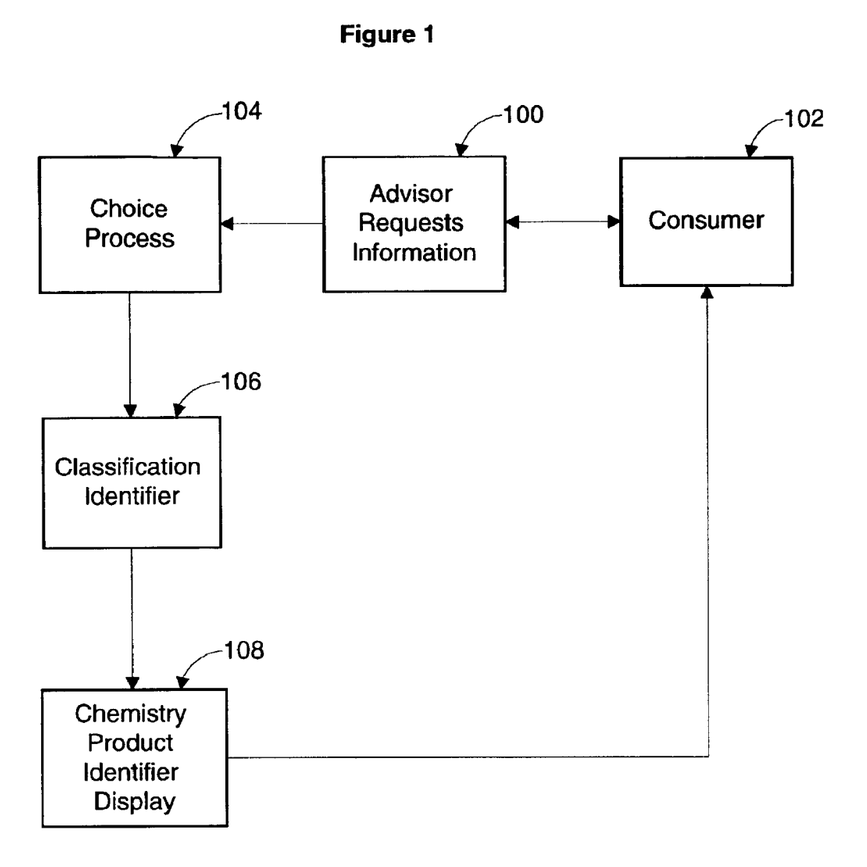
FIGS. 1–4 are flow charts of exemplary methods of the present invention.

FIG. 1 provides an overview of one method of the present invention. As indicated in block 100, an oral care selection advisor requests information regarding a consumer's oral care preferences. In one embodiment of the present invention an interactive oral care selection advisor comprises a data output device for requesting consumer oral care preference information, and a data input device by which the consumer can input the requested data. Suitable devices include, but are not limited to, keyboards, touch-screen displays, LCD screens, LED screens, CRT monitor devices, television screens, projectors, speakers, printers, as well as devices that convert visual cues to tactile producing devices (i.e., Braille), and the like. In this embodiment the interactive oral care selection device also comprises a data storage device (i.e., optical storage device, magnetic storage device, RAM, ROM, EPROM, and the like) that stores a set of selection criteria used to select an appropriate oral care classification based on the oral care preference data input by the consumer. The data storage device may optionally store information specifying which chemistries belong to specific oral care classifications. An interactive oral care selection advisor can also comprise a processor which compares the requested oral care preference information inputted by the consumer with selection criteria to select and display at least one appropriate chemistry classification.

As would be known to one of skill in the art, an oral care selection advisor can be placed proximate to an in-store display case containing a plurality of different chemistries on various shelves that contain oral care products. A display case can also comprise shelves, or bins, for prepackaged oral care products.

The oral care selection advisor can be in the form of software code that is executed in whole or in part on a generic computer connected to the World Wide Web. The consumer can receive the software code from a server over the network, or from a software storage device that contains all the necessary code to turn a generic computer into an oral care selection advisor. This can allow a consumer to purchase the selected chemistry(s) over e-commerce transaction servers and the purchased chemistry(s) can then be shipped directly to the consumer.

An exemplary oral care selection advisor can be designed as a client/server network that can be employed to implement an embodiment of the present invention. As one with ordinary skill in the art will readily appreciate, a client/server network is only one type of network, and a variety of other configurations, such as peer-to-peer connections, are also considered networks. In a client/server network, a plurality of nodes is interconnected so that the various nodes send and/or receive information to/from one another. A server node can be interconnected with a plurality of network components using a connection such as a token ring, Ethernet, telephone modem connection, radio or microwave connection, parallel cables, serial cables, coaxial cables, telephone lines, universal serial bus "USB", Firewire, Bluetooth, GPS, GLOSSNAS, LORAN, cellular, pager, fiber optics, infrared "IR", radio frequency "RF", or other wireless communications, and the like, or combinations thereof.

Any suitable mechanism may be used to request oral care preference information from the consumer. Exemplary, but non-limiting, embodiments of the oral care selection advisor include printed charts, a horizontal cylinder with a stationary outer shell and rotating inner core, rotating wheels, a series of "flip up" cards, and a rotating, 3-planar member with oral care preference information and chemistry classification and/or chemistry(s) data displayed on portions of the three planes, and a roll component on which the requested oral care preference information and corresponding chemistry classification and/or chemistry(s) data are displayed.

In another embodiment of the present invention, the oral care selection advisor is a chart displaying a two-dimensional, pre-printed matrix. The cells of the matrix represent various chemistry classifications, or alternatively, various chemistries. Printed along one axis of the matrix is a request for consumer oral care preference information (i.e., preferred end result). Printed along the remaining axis of the matrix is a second request for oral care preference information (i.e., preferred flavor). In this embodiment the consumer can input the requested information by answering appropriate questions.

It has been found desirable, when selecting oral care chemistries, to insure that the chemistry(s) selected by an oral care selection advisor are efficaciously balanced and/or compatible. Balancing and/or compatibility can be based upon several factors. These factors can include prioritized needs of a consumer, the pre-, during-, and post-use compatibilities of different chemistries, the strength of selected chemistry(s), chemistry interactions causing derived resultant flavors, an inconsistency in the number of compartments present in an oral care device (discussed infra) and the number of classifications desired by a consumer, consumer financially-based considerations, and the like.

For example, an oral care selection advisor interaction may find a consumer desiring to have a high-strength pumpkin flavor chemistry and low-strength tartar control chemistry. Hypothetically, the characteristics of these two chemistries may be incompatible at these dosage levels. The oral care selection advisor could lower the high-strength pumpkin flavor chemistry to a low-strength pumpkin flavor chemistry because tartar control may provide a more efficacious benefit. In this manner, the oral care selection advisor can contain information regarding known or potential negative chemistry interactions. Thus, the oral care selection advisor assists the consumer who is unknowledgeable about oral care chemistry interactions.

In another non-limiting example, an oral care device, discussed infra, has the ability to contain only four oral care chemistry classifications. A consumer has selected five chemistry classifications including a brightening chemistry and a whitening chemistry. In this instance, the oral care selection advisor can determine that five oral care chemistry classifications have been chosen for an oral care device having only four compartments and advise elimination of a lower priority (brightening), or less efficacious, chemistry from the advised options.

It is believed that many potentially efficacious combinations of oral care chemistry(s) are unavailable in current oral care selection processes because of the complexity of, the number of oral care chemistries needed to be available, and the potential for consumer selection error. Thus, it is within the scope of the present invention that a lock and key is provided. The lock and key can be used if a consumer omits the use of an oral care selection advisor in order to self-select the strongest of all desired and/or available chemistries. A lock and key can provide a safeguard in instances where self-selection of oral care chemistries can produce a deleterious effect. Such deleterious effects can range from minor temporary negative tastes to more serious tooth staining, increased sensitivity, and the like.

Referring again to FIG. 1, once the oral care preference information has been requested and input by the consumer, block 102, the oral care selection advisor selects an appropriate chemistry classification, block 104. In one embodiment of the present invention an interactive oral care selection advisor is used that matches the oral care preference information input, against a set of chemistry classification selection criteria.

Figure 4:
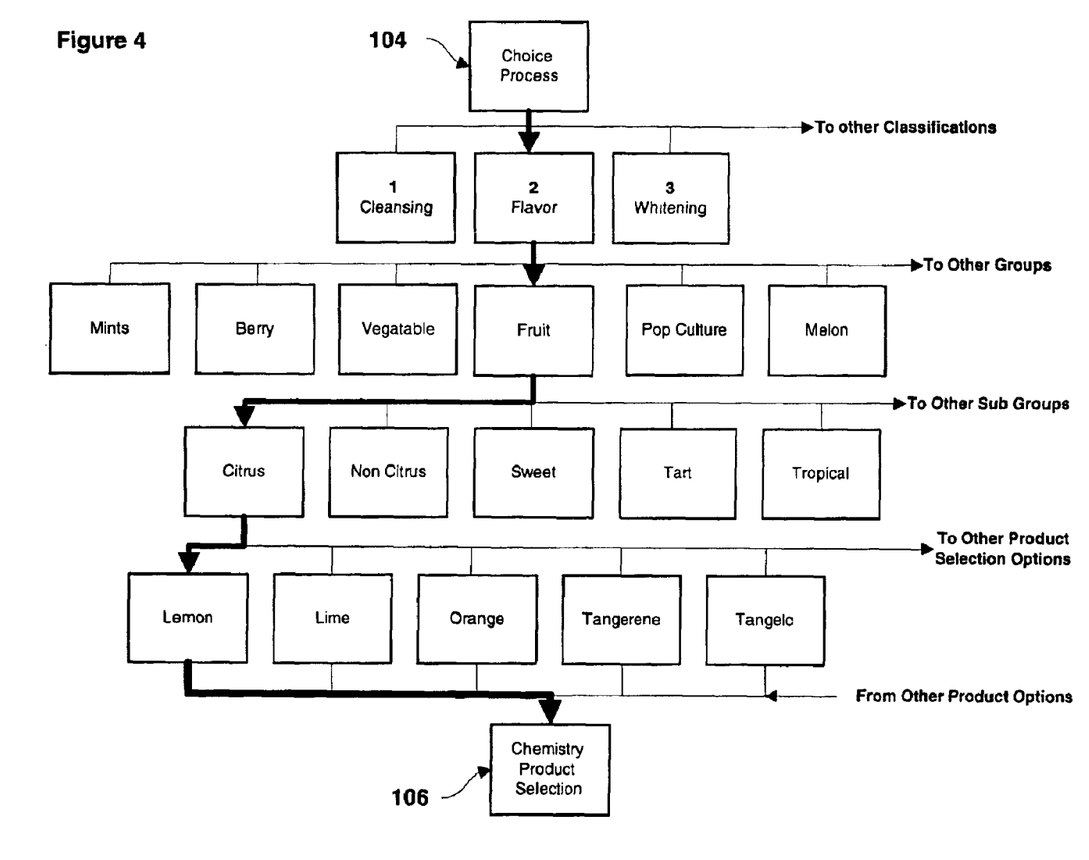

The oral care classification selection criteria to provide custom-tailored oral care chemistry(s) could be a decision tree, or optionally a set of look-up tables. As shown in FIG. 4, a decision tree can comprise a set of responses/traits/categories against which the consumer oral care preference data can be compared. For example, a decision tree might comprise some combination, or every combination, of possible consumer oral care preference data. The oral care preference data are then compared against the decision tree in order to provide further instructions to be executed as a result of the match. Such decision trees would preferably comprise potential combinations of consumer oral care preference data that have been designed to optimize the selection process in order to obtain the optimal classifications and/or chemistry(s) for the consumer. As would be known to one of skill in the art, the decision trees can be converted to mathematical algorithms, which can then process the decision tree comparisons or "decisions" electronically to quickly ascertain the appropriate optimized chemistry formulation for the oral care delivery system.

FIG. 4 depicts an exemplary, but non-limiting, application for the selection of a particular oral care chemistry identifier upon the selection of an oral care chemistry classification. A consumer is presented with a plurality of oral care chemistry classifications including, but not limited to: cleansing, flavoring, and whitening. Upon the selection of a flavoring classification, the consumer is presented with a plurality of group choices available within the flavoring classification, including, but not limited to: mints, berry, vegetable, fruit, pop culture, and melon. Upon the selection of the fruit group choice, the consumer is then prompted to select from a fruit group sub-group, including, but not limited to: citrus, non-citrus, sweet, tart, and tropical. Upon the selection of a citrus sub-group, the consumer is presented with a plurality of sub-group product options including, but not limited to: lemon, lime, orange, tangerine, and tangelo. Upon the selection of the lemon product, the oral care selection advisor can then proceed to display the identifier corresponding to the consumer selected lemon flavoring. One of skill in the art would be able to provide a plurality of oral care selection advisor choice options that can be individually tailored to meet the needs of the consumer.

In order to update the optimization process to allow for modification or "morphing" as appropriate, one embodiment of the present invention comprises the decision trees or algorithms of the oral care selection advisor being updated by a neural network. According to Haykin, S., *Neural Networks: A Comprehensive Foundation*, NY: Macmillan, p. 2 (1994), a neural network is a massively parallel distributed processor that has a natural propensity for storing experiential knowledge and making it available for use. It resembles the brain in two respects: 1) Knowledge is acquired by the network through a learning process; and 2) Interneuron connection strengths known as synaptic weights are used to store the knowledge. The neural network analyzes the data trends, feedback data, consumer oral care preference data and other additional data to develop and refine algorithms for decision making, for example, determine the specific type, or concentration, of a particular chemistry that would be optimal for the consumer. In another embodiment, the neural network could assess various applicable consumer oral care preference data and feedback data retrieved from the data store to determine if changes to any mathematical algorithms (dialog scripts), discussed supra, are needed to facilitate or optimize the decision making process of determining appropriate chemistry classifications and/or chemistry(s). For example, a neural network can continuously update its decision making algorithm by incorporating user input such as feedback into the decision making process akin to artificial intelligence or "smart" logic. In one embodiment, a neural network would automatically make changes to the oral care selection advisor's decision trees or algorithms based upon the growing base of consumer need and user feedback data.

Referring again to FIG. 1, once the appropriate chemistry classification has been selected, the oral care selection advisor displays a chemistry classification identifier corresponding to the selected chemistry classifications, block 106. This chemistry classification identifier can be comprised of at least one identification element such as a classification name or another written word or group of words, an icon or set of icons, a color, a pattern, a sound, tactile impression, an aroma, or any combination thereof, and the like. The requirement is that each chemistry classification identifier be different from other identifiers.

Finally, the oral care treatment selection advisor displays the chemistry product identifier corresponding to the selected chemistry classification, block 108. As with the chemistry classification identifier above, the chemistry identifier can be unique.

Figure 2:
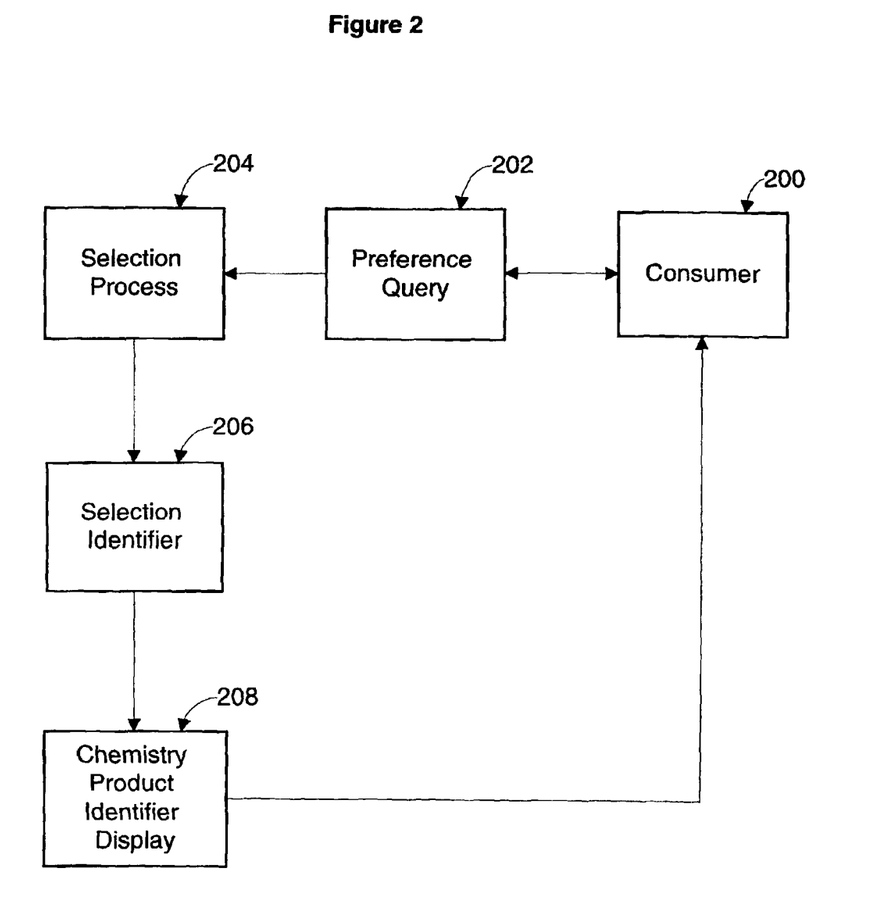

In another exemplary embodiment as shown in FIG. 2, oral care preference information is requested from the consumer, block 200. The consumer then inputs the requested oral care preference information in a manner consistent with the type of oral care selection advisor being employed, block 202. The oral care selection advisor compares the oral care preference information requested of the consumer and matches that information against a set of oral care treatment product selection criteria, block 204. The oral care selection advisor then selects at least one appropriate chemistry, block 206, and then displays, in a manner consistent with the type of oral care selection advisor employed, a chemistry product identifier, comprising one or more identification elements, for at least one chemistry, block 208.

Figure 3:
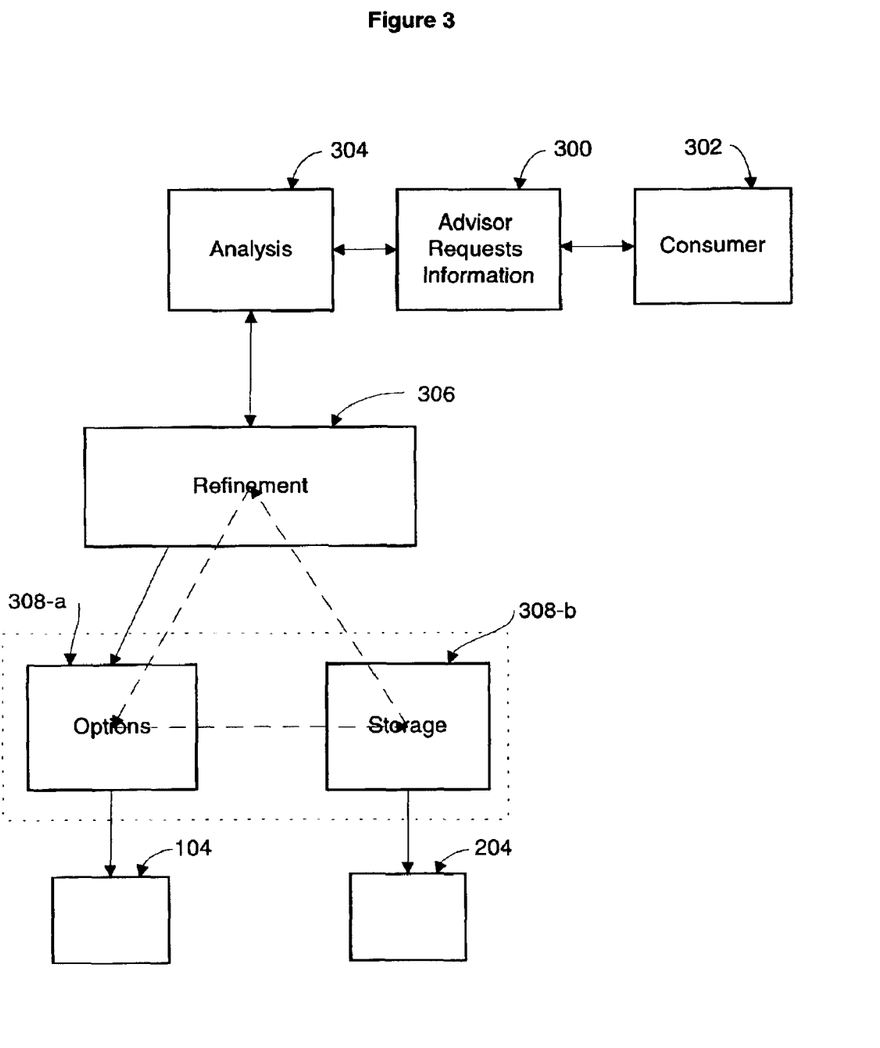

FIG. 3 provides an overview of the process detailing how either the oral care classification selection criteria and/or chemistry selection criteria can be further refined and updated. In block 300, consumer oral care preference information is requested from the consumer. The consumer then inputs the requested oral care preference information in a manner consistent with the type of oral care selection advisor being employed, block 302. The oral care selection advisor analyzes the requested oral care preference information, block 304, and refines the appropriate selection criteria (i.e., asks for additional consumer input), block 306. In optional block 308, the oral care selection advisor may reapply 308*a* the refined selection criteria or it may store 308*b* the refined selection criteria for review and subsequent use.

After receiving information from a consumer, or other third party, regarding the consumer's oral care preferences, comparing that information against the selection criteria and having selected a classification of chemistry(s) from at least one available classification, preferably up to at least about 9 classifications, the method of the present invention calls for displaying information back to the consumer, caretaker, insurance company, or other third party, identifying the chemistry(s) which make up the chemistry classification, thereby allowing the consumer to purchase the chemistry(s), or other products. This provision of information may be provided through the use of packaging indicia. For example, in a preferred embodiment with three available classifications of chemistries, each system may have an associated unique number, color, symbol, or combination thereof. Chemistries that make up each of the classifications could then be packaged in packages marked with the corresponding unique number, color, symbol, or combination thereof. Further, chemistries that comprise each classification can be mixed prior to packaging or prior to, or at, the time of sale.

Exemplary, but non-limiting, classifications of chemistries can include flavors, cleansers, educational agents, appearance, form, tooth treatments, medications, breath fresheners, an open class, and combinations thereof. Exemplary flavors can include mints (e.g. spearmint and peppermint), tropical flavors, citrus fruits (e.g. lemon, lime, orange, and tangerine), other fruits (e.g., wild cherry, cherry, and grape), wintergreen, chocolate, coffee, holiday-based flavors (e.g., pumpkin at Halloween), sassafras, berries (e.g. blueberry, strawberry, and huckleberry), and combinations thereof. Exemplary cleansers can include tartar control, light cleansers, medium (average) cleansers, heavy (deep) cleansers, neglected oral hygiene cleansers, youth strength cleansers, and combinations thereof. Exemplary educational chemistries can include predisclosers (e.g., prior to cleansing), disclosers (e.g., after cleansing), and combinations thereof. Predisclosers and disclosers comprise the procedure and materials of use that define a procedure where a user can identify areas of the oral cavity, in particular the teeth and gums, that have received less than adequate oral care treatment. As would be known to one of skill in the art, a tinted liquid, solid, gel, or paste may be distributed throughout the oral cavity and adheres to food particulate and residue. This can provide an identifiable guide for the user to provide enhanced oral care to the area of interest.

Exemplary appearance chemistries can include sparkles, stripes, polka dots, monocolors, pastels, and combinations thereof. Exemplary form chemistries can include gels, pastes, liquids, aerosols, mists, foams, mild-, medium-, heavy-, and non-suds generating chemistries, and combinations thereof. Exemplary tooth treatments can include sealants, fluorides, whitenings, and combinations thereof. Exemplary medications can include gingivitis treatments, temperature sensitivity reduction treatments, chemistry sensitivity reduction treatments, and combinations thereof. Exemplary breath treatment chemistries can include spearmint, peppermint, original (no flavors), mouthwash, citrus aromas, other fruit aromas, and combinations thereof. The open class chemistries can include modified chemistries, such as prescription, or alternate strengths, that can provide an "over-the-counter" equivalent chemistry first provided by any professional care provider.

In another embodiment of the present invention, the multiple chemistry(s) making up a given classification can be sold, and/or packaged together in a common package. This allows a consumer to purchase an entire classification in a "sampler pack" format without having to separately gather the required products.

In a further embodiment of the present invention, it is believed that an oral care device can be provided with at least one compartment, and optional instructions for use, that provides a method for the consumer selection of chemistry(s). It is believed that each compartment within an oral care device can be provided with, or contain, chemistry(s) as described supra. For example, the selection of the total amount of chemistry(s) needed to operate an oral care device and provide the oral care benefits can be based on a consumer choosing a particular chemistry(s) for a specific compartment within the device.

It is believed that each compartment of an oral care device can require that a particular chemistry be in place to allow operation of the device. It is also believed that each compartment of the device can be provided with indicia to aid the consumer in selection and placement of a selected chemistry(s) within the device. Exemplary, but non-limiting indicia can include coding with a number, letter, color, geometry, or a combination thereof. In a preferred embodiment, a consumer can find and select a chemistry(s) as provided by the indicia located proximate to an oral care device from exemplary chemistry classifications or chemistry(s) displayed on a store shelf proximate to a selection of oral care devices.

A plurality of oral care devices can be manufactured to assist the consumer selection of a particular oral care device tailored to a corresponding chemistry classification or chemistry(s). The device selection, performed in a manner similar to the methods of chemistry selection as discussed supra, can be based upon price point (e.g., both of the oral care device and number of chemistry(s) required to operate), trial (e.g., simplified selection processes to provide consumer impetus to try the oral care device), sampling (e.g., a low cost method to provide a low-cost, or free, oral care device to potential consumers or a professional health care provider, or industry), graduated use (e.g., the consumer can 'move up' to more features and benefits as necessary), prescriptory (e.g., prepackaged chemistry(s) to meet a medicinal prescription as provided by a health care professional), and/or combinations thereof.

It is also believed that the operation of an oral care device can be prevented if excess, or insufficient, quantities of the same chemistry classification or chemistry(s) are present. A treatment regimen that is missing chemistry(s) could result in no end benefit to the user, damage to the oral tissue and/or teeth, or other undesired/negative results.

By way of example, a user may incorrectly believe that some benefit can be obtained from using the oral care device, even if one chemistry of a treatment regimen is depleted, or in which two or more chemistries are used in an inefficacious order. Alternatively, a user may incorrectly believe that even though a prescribed quantity of oral care chemistry provides a satisfactory result, using more of that particular chemistry must be better, when it is not. In any regard, it may be possible for incorrect chemistries, negatively interacting chemistries, missing chemistries, or excess chemistries, to exhibit undesireable effects. For instance, some oral care chemistries may not be compatible during storage and require mixing directly prior to, or at the time of, use.

Thus, it can be beneficial to provide an oral care device with physical, and/or electronic, indicia, such as a 'lock and key.' The lock and key can require more than one chemistry(s) to be placed in the oral care device to allow operation. This can include chemistry(s) that are dosed, dispensed, and/or mixed immediately at the point of use by the oral care device (e.g., at a brush, or applicator, tip).

Exemplary, but non-limiting embodiments of lock and key indicia can include active-, and passive physical features, and active-, passive-, and intelligent electronic circuitry. Exemplary circuitry can be located within in the oral care device to read output from a sensor located proximate to a chemistry cartridge. Alternatively, circuitry could be provided on each chemistry cartridge to enable each chemistry cartridge to identify each other and provide programming directives to the oral care device.

An exemplary active physical feature includes an integral tab present on a chemistry cartridge that is capable of activating the oral care device when positioned within the oral care device (i.e., tab 'A' of cartridge 'A' must be in slot 'A' of the oral care device). An exemplary a passive physical feature can include a tab located in a chemistry-specific location on a chemistry cartridge so that an operational interference to the oral care device is caused if more, or less, than the intended number of chemistry cartridges are present, or are present in an incorrect chamber (i.e., tab 'A' of cartridge 'A' physically interferes with another tab 'A' of cartridge 'A' if another cartridge 'A' were placed within an oral care device). Exemplary active-, and passive electronic circuitry can provide sensors to sense that the correct number of chemistry cartridges is present in appropriate positions within an oral care device. Exemplary intelligent electronic circuitry can identify each inserted chemistry cartridge, its location within an oral care device, and as would be known to one of skill in the art, compare this information to a database, algorithm, or artificial intelligence system that can then program the oral care device to dispense only the correct chemistries, in the correct combinations, and/or sequences, in a safe and efficacious manner.

While particular embodiments of the present invention have been illustrated and described, it would be obvious to those skilled in the art that various other changes and modifications can be made without departing from the spirit and scope of the invention. Any of the aspects of the invention of the present invention found to offer advantages over the state of the art may be used separately or in any suitable combination to achieve some or all of the benefits of the invention disclosed herein.

What is claimed is:

1. A method for the selection of an oral care treatment from a plurality of options, said method comprising the steps of:
   (a) requesting information from a consumer regarding said consumer's oral care preferences, said request of said information being accomplished with an oral care selection advisor, wherein said oral care selection advisor selects a classification of chemistries from among at least two available classifications, each of said classifications comprising one or more different chemistry(s), wherein each of said available classifications corresponds to said consumer's oral care preferences and/or aspirations; and
   (b) displaying information from said oral care selection advisor identifying each of said chemistry within each of said selected classifications, thereby indicating said chemistries corresponding to said consumer's oral care preferences, wherein the combination of said chemistries comprises a treatment regimen.

2. The method of claim 1, wherein said oral care selection advisor is located proximate to a display case containing at least one of said chemistries within each of said available classifications.

3. The method of claim 1, wherein said oral care selection advisor is capable of preventing a selection of a first classification of chemistry from said at least two available classifications when said first classification of chemistry is incompatible with a selected second classification of chemistry from said at least two available classifications.

4. The method of claim 1, wherein said oral care selection advisor is capable of sequencing said at least two available classifications of said oral care treatment regimen.

5. The method of claim 1, wherein said consumer is selected from the group consisting of a purchasing agent, an end user, a consumer's caretaker, a consumer's patent, a consumer's dentician, a consumer's insurance carrier, a consumer's health care professional, merchant, or other person engaged in the recommendation, retail sale, promotion, distribution, giveaway, or trade of oral care products, and combinations thereof.

6. The method of claim 1, wherein said chemistries corresponding to said consumer's oral care preferences are at least partially insertable into an oral care device having at least one compartment therein.

7. The method of claim 6, wherein said oral care selection advisor is capable of preventing a selection of a first classification of chemistry from said at least two available classifications upon said consumer selecting a number of said consumer's oral care preferences and/or aspirations that is greater than the number of compartments available in said oral care device.

8. The method of claim 6, wherein said oral care selection advisor is capable of requiring an additional selection of a first classification of chemistry from said at least two available classifications upon said consumer selecting a number of said consumer's oral care preferences and/or aspirations that is less than the number of compartments available in said oral care device.

9. The method of claim 1, wherein said oral care selection advisor selects a concentration of said one or more different chemistry(s) in response to said consumer's oral care preferences and/or aspirations.

10. The method of claim 9, wherein said oral care selection advisor is capable of selecting a more efficacious concentration of said one or more different chemistry(s) when said concentration of said one or more different chemistry(s) is not capable of providing an efficacious result for said consumer.

11. The method of claim 9, wherein said oral care selection advisor is capable of selecting a more efficacious concentration of said first classification of chemistry from said at least two available classifications when said first classification of chemistry is chemically incompatible with a second classification of chemistry from said at least two available classifications.

12. A method for the selection of an oral care treatment from a plurality of options, said method comprising the steps of:
   (a) providing at least two available classifications of chemistries, said at least two available classifications of chemistries comprising a treatment regimen;
   (b) selecting an oral care device having at least one compartment disposed therein, said at least one compartment corresponding to a classification of chemistries from among said at least two available classifications of chemistries, each of said at least two available classifications of chemistries comprising at least one chemistry, each of said at least two available classifications of chemistries corresponding to a consumer's oral care preferences, said at least one compartment having indicia disposed thereon, said indica being provided as a geometry for said at least one compartment, said indicia designating one of said classifications;
   (c) placing said at least one chemistry into said at least one compartment of said oral care device; and,
   wherein said geometry is capable of preventing insertion of said at least one chemistry when said at least one chemistry is incompatible with classification.

13. The method of claim 12, wherein said at least one chemistry is selected to provide a prescribed oral care treatment regimen.

14. The method of claim 12, wherein said at least one compartment is provided with at least one chemistry corresponding to said consumer's oral care preferences.

* * * * *

UNITED STATES PATENT AND TRADEMARK OFFICE
CERTIFICATE OF CORRECTION

PATENT NO.    : 6,890,182 B2                                      Page 1 of 1
DATED         : May 10, 2005
INVENTOR(S)   : Healey et al.

It is certified that error appears in the above-identified patent and that said Letters Patent is hereby corrected as shown below:

Column 11,
Line 62, "patent" should be -- parent --.

Signed and Sealed this

Thirtieth Day of August, 2005

JON W. DUDAS
*Director of the United States Patent and Trademark Office*